United States Patent [19]

Lechner et al.

[11] Patent Number: 4,714,467
[45] Date of Patent: Dec. 22, 1987

[54] REINFORCED FIBER BONE REPLACEMENT IMPLANT HAVING TREATED SURFACES AND A METHOD FOR ITS MANUFACTURE

[75] Inventors: Fritz Lechner, Garmisch-Partenkirchen; Herbert Heissler, Munich; Wolfgang Scheer, Holzkirchen; Wolfgang Siebels, Munich; Rudolf Ascherl, Garmisch-Partenkirchen, all of Fed. Rep. of Germany

[73] Assignee: M A N Technologie GmbH, Munich, Fed. Rep. of Germany

[21] Appl. No.: 843,733

[22] Filed: Mar. 25, 1986

[30] Foreign Application Priority Data

Mar. 30, 1985 [DE] Fed. Rep. of Germany ....... 3511779
Jul. 5, 1985 [DE] Fed. Rep. of Germany ....... 3524020

[51] Int. Cl.[4] .................... A61F 2/36; B29C 67/14; B65H 81/00
[52] U.S. Cl. ...................... 623/16; 264/137; 264/139; 523/219; 623/18; 623/22; 623/23
[58] Field of Search ............ 264/137, 139; 523/219; 623/23, 22, 16, 18, 1

[56] References Cited

U.S. PATENT DOCUMENTS

| | | | |
|---|---|---|---|
| 2,382,248 | 8/1945 | Mason | 264/139 X |
| 3,848,273 | 11/1974 | Frey | 623/23 |
| 3,938,198 | 2/1976 | Kahn et al. | 623/23 X |
| 4,055,862 | 11/1977 | Farling | 623/22 X |
| 4,064,567 | 12/1977 | Burstein et al. | 623/23 X |
| 4,129,470 | 12/1978 | Homsy | 623/23 X |
| 4,164,794 | 8/1979 | Spector et al. | 623/18 X |
| 4,221,623 | 9/1980 | Heissler et al. | 623/23 X |
| 4,356,571 | 11/1982 | Esper et al. | 623/18 X |
| 4,411,027 | 10/1983 | Alexander et al. | 623/16 X |
| 4,605,416 | 8/1986 | Grobbelaar | 623/23 |

FOREIGN PATENT DOCUMENTS

| | | | |
|---|---|---|---|
| 0019043 | 11/1980 | European Pat. Off. | 623/22 |
| 0019044 | 11/1980 | European Pat. Off. | 623/22 |
| 0057033 | 8/1982 | European Pat. Off. | 623/DIG. 1 |
| 2502884 | 7/1976 | Fed. Rep. of Germany | 623/22 |
| 59-201840 | 11/1984 | Japan | 264/139 |

*Primary Examiner*—Philip Anderson
*Attorney, Agent, or Firm*—Alan H. Levine

[57] ABSTRACT

In a method of producing implants of bone replacement material from resin reinforced with carbon fiber at least the fibers in the parts of the surface which are to come into contact with the bone tissue are exposed by mechanical treatment. This provides for an improved unification of the bone with the implant. The fibers at the surface may be fibers of a fabric which is wrapped around a basic member shaped to conform to the desired implant.

9 Claims, 4 Drawing Figures

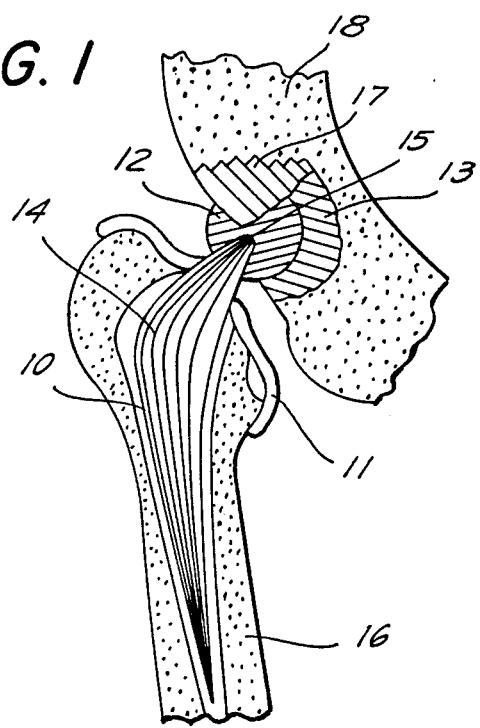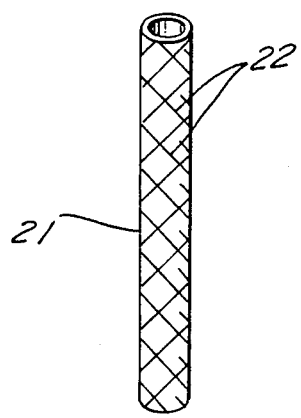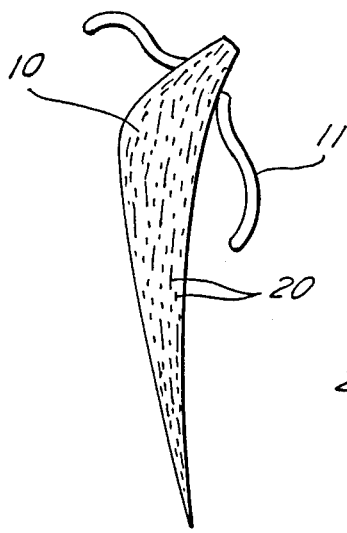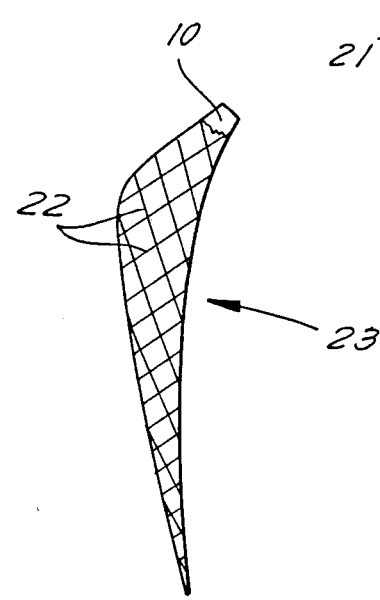

REINFORCED FIBER BONE REPLACEMENT IMPLANT HAVING TREATED SURFACES AND A METHOD FOR ITS MANUFACTURE

BACKGROUND OF THE INVENTION

The invention relates to bone implants and more especially to a method for the production of bone replacement implants made of resin reinforced with fiber.

The purpose of the development of replacement bone implants is to provide patients with an efficient support for bone structures which are no longer able to perform their proper function for rest of the patient's life.

In the prior art implants have been bonded in place by means of a bicompatible bonding material in the bone cavity in question. However it has been found that owing to the high loads an implant treated in this way works loose and becomes detached from the attaching means.

SHORT SUMMARY OF THE PRESENT INVENTION

One object of the present invention is to devise a method of the initially specified type which makes it possible for implants to have a longer working life.

In order to achieve this or other aims appearing in the course of the present specification, after the production of the fiber reinforced resin member the surface is treated at least in part until the fibers are at least partly exposed.

In accordance with another aspect, in the present invention a basic fiber reinforced member having the form of the implant is produced with its fibers essentially extending in a single direction, the basic member is so wrapped with a piece of fabric made up of fibers or single filaments impregnated with matrix material that the fibers of the fabric intersect those of the basic member and the composite structure made up of the basic member and the fabric is pressed to shape it and after curing of the matrix surface of the implant produced in this way is so treated that the fibers are at least partly exposed.

It has been seen from tests that the exposed fibers provide an improved basis for the unification of the bone around the implant. In this respect the anchoring effect is simultaneously enhanced inasmuch as there is no intermediate layer of adhesive which might crumble and leave a gap between the bone and the implant.

The use of the form of the method involving the wrapping in fabric offers the additional advantage that the orientation of the fiber achieves a high compressive and torsion strength which is resistant to heavy loads and is therefore able to counteract any effects that would otherwise impair the incorporation of the implanted prothesis in the bone and its unification therewith. This is particularly signficant in the case of the shank of a prosthesis used as an artificial joint. This part of the invention is characterized in that above-mentioned advantage is able to be achieved with simple production methods inasfar as the implant is produced by combining two parts with different fiber orientations. The basic member is produced with fibers that are preferably unidirectional and aligned with the direction of compressive loading, whereas the resistance to torsion is produced by the separately produced fabric, whose fibers form intersecting layers on the implant as necessary for the resistance to torsion.

In order to enhance joining by growth use is preferably made of carbon fibers which are embedded in a matrix of polyphenolglycidylether and 4,4'-diaminodiphenylsulphone. As experiments and tests have shown, such materials have a good compatibility with the body tissue so that owing to the materials and the nature of the surface the implant may be directly surrounded by the bone tissue and this encourages growth. This takes place without having to utilize intermediate layers which are prone to become detached from the implant so that there is an additional risk factor.

More particularly in the case of implants made by pressing it is possible, in accordance with a further feature of the invention, to mechanically treat the implant, as for example by roughening after the curing of the matrix material in order to expose the fibers.

If the implant is produced by a method involving shaping by a mechanical processes, the shaping may be carried out in such a way that it simultaneously exposes or uncovers the fibers on the surface. Such a method may be by milling.

The fabric is preferably made of carbon fibers as well and impregnated with polyphenolglycidylether and 4,4'diaminodyphenylsulfone and the surface treated, to expose the fibers, by roughening.

One more especially preferred application of the method of the invention is in the form of a joint prosthesis consisting of a shank with a joint ball joined thereto for cooperation with a joint socket. In the case of such a prosthesis the shank part to be introduced into the bone and the rear surface of the joint socket are to be treated to expose the fibers.

In order to ensure that the good incorporation properties, which increase the length of life of an artificial joint, are not mitigated against by "points of weakness" there is the further proposal of the invention that the shank of the prosthesis be provided with a supporting collar of a part protruding from the bone and with a joint ball of ceramic, as for example of aluminum oxide or silicon nitride. In this respect the joint socket should have a thread so that the socket may be screwed in place and thus anchored more securely. These features in conjunction with the surface treatment increase the length of life of the implant for joints.

The supporting collar for the shank substantially prevents axial displacement or friction so that there is the very least interference with the incorporation process. Furthermore the point of articulation itself is very relevant as regards the durability of an artificial joint. The joint as well should be so contrived that it does not reduce the durability of the anchoring effect. It has been proved that the specific choice of materials so as to have a ceramic ball on the one hand and a socket made of the above-noted composite material reinforced with carbon fiber is such that there is substantially no abrasion to be noted. As for the shank, the fabric may be produced in the form of a flexible tube and drawn over the shank, the tube being considerably stretched at the thicker end of the shank so that the fibers are pulled into a taut condition as is in fact desired. The only other way of producing such a taut condition would be by winding.

The invention will now be described with reference to the drawings.

LIST OF THE SEVERAL VIEWS OF THE DRAWINGS

FIG. 1 shows a hip joint implant.

FIG. 2 shows a further view of the implant before insertion.

FIG. 3 shows a wound tube.

FIG. 4 shows the shank of the implant with the fabric wrapped onto it.

DETAILED ACCOUNT OF EMBODIMENTS OF THE INVENTION

The hip joint implant to be seen in FIG. 1 consists of a shank 10 with a support collar 11 and a joint ball 12. There is furthermore a joint socket 13. The shank 10 is reinforced with carbon fibers 14 that are unidirectional and more or less parallel to the outer face of the shank 10 so that this part of the prosthesis is endowed with sufficient stiffness to effectively resist the load or stress that is predominantly in the axial direction.

The upper end 15 of the shank 10 is made conical in form so as to fit into the joint ball 12 or in other words the ball 12 is plugged onto the conical end 12. In order to ensure the best possible bearing properties between the joint head 12 and the joint socket 13 the joint head 12 is made of ceramic material and the joint socket 13 is made of a carbon fiber reinforced material with a matrix of polyphenolglycidylether and 4,4'-diaminodiphenylsulfone.

In order to minimize slipping of the shank 10 within the femur shank 16 under an axial load, the support collar 11 is so arranged on the shank 10 that it rests on the upper end of the femur 16. To ensure secure mounting of the joint socket 13 there is a thread thereon to enable the socket 13 to be screwed into the pelvis 18.

The features of the prosthesis described so far serve to provide a strong and as far as possible permanent attachment in the bone. However, as such these features are not sufficient to provide for a secure and fully functional supporting effect for the lifetime of the patient. In fact, a further important point is to prevent the prosthesis being rejected by the human organism as a foreign body. A high level of compatability is ensured by the choice of material, while to encourage unification of the bone around the implant an external treatment of the contact faces of the implant with the bone is employed. This treatment involves so roughening the surface of the shank below the support collar 11 that, as shown in FIG. 2, fibers 20 are exposed. Owing to the good compatibility of the carbon fibers with the body these fibers enable an initial connection to be made with the bone material with the outcome that there is an improved growth of the bone unification around the shank 10.

The uncovering of the fibers and fiber ends 20 may be undertaken in a number of different ways. The uncovering of the fibers of the joint socket 13 may for example take place directly in conjunction with milling or routing the thread 17.

The exposed carbon fibers 20 that are compatible with the body tissues, have a substantial effect in promoting unification of the bone material around the implant. This process of unification may be supported by ensuring the least relative motion between the prothesis part and the bone. This may be achieved by the combination of the following features; the high degree of stiffness owing to the selection of fibers of carbon and their alignment in the shank 10, the supporting effect of the support collar 11 on the shank 10, the small gap, that may be maintained, between the joint ball 12 and the joint socket 13 owing to the good sliding or self-lubricating properties, and the screw thread for anchoring the joint socket 13 in place.

If the implant 10 is made by simple production technology with solely unidirectional fibers 14 it is possible to apply a layer of fibers with a different alignment by separately producing a piece of fabric, preferably in the form of a flexible tube 21, which is impregnated with a matrix material and is then drawn onto the implant member 10. The fabric 21 is applied in such a way that its fibers run obliquely in relation to the fiber direction of the basic member and the fibers 14 and 22 of the composite structure are generally aligned with the direction of load thereon.

For the basic member 10 the fibers 22 of the fabric tube 21 run obliquely in relation to the longitudinal axis of the tube so that the same has a certain degree of stretch. On application of the tube 21 to the basic member 10 in the thicker part of the member in which the tube is stretched, the fibers 22 approximately assume the desired orientation of about 45°. This angle decreases towards the end down to about 15° to 20°.

We claim:

1. A bone replacement implant comprising a resin body having embedded within it reinforcement fibers, the surface of the body being roughened, and ends of at least some of the reinforcement fibers being exposed on the surface of the body.

2. A method of making a bone replacement implant, comprising the steps of:
    forming an implant member solely of a resin containing reinforcement fibers, and
    treating the surface of the member to remove some of the resin therefrom, sufficient resin being removed so as to roughen the surface and expose some of the fibers on the surface of the implant, thereby enhancing the ability of the implant surface to fuse directly with human bone tissue.

3. A method as defined in claim 1 wherein the surface treatment of the implant member involves mechanically working the surface.

4. A method as defined in claim 2 wherein the surface treatment of the implant member involves mechanically working the surface to give the implant its final shape.

5. A method as defined in claim 2 wherein the surface treatment of the implant member is effected by milling the surface.

6. A method as defined in claim 2 wherein the bone replacement implant includes a hip joint prosthesis having a shank, the reinforcement fibers being arranged unidirectionally and generally axially within the resin of the shank and approximtely parallel to the outer surface of the shank.

7. A method as defined in claim 6 including the step of placing a fabric tube over the shank of the implant member prior to treating its surface, the tube comprising carbon fibers impregnated with a resin, and the fibers being oriented generally obliquely to the fibers within the shank.

8. A method as defined in claim 2 including the step of placing a fabric tube over the implant member prior to treating its surface, the tube comprising carbon fibers impregnated with a resin, and the surface treatment serving to remove some of the resin of the fabric tube to expose some of the fibers of the tube.

9. A method as defined in claim 2 wherein the bone replacement implant includes a hip joint prosthesis having a shank, and including the step of providing a support collar on the shank in a position to engage the end of the bone into which the shank is inserted.

* * * * *